US005636286A

United States Patent [19]

Makabe et al.

[11] Patent Number: 5,636,286

[45] Date of Patent: Jun. 3, 1997

[54] ACTIVE NOISE REDUCTION DEVICE FOR ELECTRONIC APPARATUS

[75] Inventors: Eiji Makabe; Tsutomu Hoshino; Atsushi Yamaguchi; Tadashi Ohashi, all of Kawasaki, Japan

[73] Assignee: Fujitsu Limited, Kawasaki, Japan

[21] Appl. No.: 289,588

[22] Filed: Aug. 15, 1994

[30] Foreign Application Priority Data

Oct. 1, 1993 [JP] Japan .................................... 5-269523

[51] Int. Cl.$^{6}$ ............................ A61F 11/06; H03B 29/00

[52] U.S. Cl. ............................ 381/71; 381/94; 181/216; 181/224

[58] Field of Search ............................ 312/223.1, 223.2, 312/100, 257.1, 265.5, 265.6; 381/71, 94; 181/216, 224

[56] References Cited

U.S. PATENT DOCUMENTS

| | | | |
|---|---|---|---|
| 4,672,509 | 6/1987 | Speraw | 361/695 |
| 4,677,677 | 6/1987 | Eriksson | 381/71 |

FOREIGN PATENT DOCUMENTS

| | | | |
|---|---|---|---|
| 0232973 | 9/1993 | Japan . | |
| 0161475 | 7/1994 | Japan | 381/71 |

*Primary Examiner*—Curtis Kuntz
*Assistant Examiner*—Duc Nguyen
*Attorney, Agent, or Firm*—Staas & Halsey

[57] ABSTRACT

An active noise reduction device for reducing the noise produced by cooling fans in a computer. The active noise reduction device comprises a duct mounted on the casing of the computer and having at least one air passage. One end of the passage communicates with the interior of the casing near the cooling fans and the other end is open to the atmosphere. A first microphone is arranged in the duct near the first end opening for detecting noise, and a second microphone is arranged in the duct near the second end opening. A speaker is arranged in the duct near the second opening, and a controller controls the speaker in response to outputs of the first and second microphones for reducing the noise produced in the casing. The speaker makes a sound having a reverse phase to that of the noise produced in the computer and the speaker sound is superimposed on the noise.

19 Claims, 9 Drawing Sheets

ACTIVE NOISE REDUCTION DEVICE FOR ELECTRONIC APPARATUS

BACKGROUND OF THE INVENTION

1. Field of the Invention

The present invention relates to an active noise reduction device for reducing the noise produced in an electronic apparatus such as a computer.

2. Description of the Related Art

An electronic computer comprises a casing (cabinet) and various electronic components arranged in the casing. The electronic components usually produce heat and the temperature in the casing rises. A cooling fan (or cooling fans) is thus arranged in the casing to convey heat to the outside of the casing. In particular, fresh air is sucked into the casing via an air inlet, and forcibly blown through the casing by the cooling fan to cool the electronic components, the hot air being exhausted from the casing via an air outlet. In such an apparatus, the cooling fan produces noise which leaks i.e., is transmitted, to the outside of the casing via the air inlet and the air outlet. Therefore, the working environment in an office in which the computer is used is affected adversely.

To actively reduce noise, it is known to use an active noise reduction device in a structure. The active noise reduction device can reduce a noise by making a sound having a waveform with the same amplitude as that of the noise but with the opposite phase of the noise, the sound being superposed on the noise. In the conventional active noise reduction device, the noise is introduced into a special duct. A microphone is arranged in the duct near the inlet thereof for detecting the noise. A digital filter generates a noise reducing signal in response to the output of the microphone, and a speaker is arranged in the duct near the outlet of the duct. The speaker makes a sound based on the noise reducing signal and the sound has a waveform with the same amplitude as that of the noise but in the opposite phase of the noise. The sound is superposed on the noise propagating in the duct to thereby reduce the noise.

The conventional active noise reduction device, for example, is built in an air conditioning system including a duct extending along the ceiling of a building structure for reducing a noise induced by a flow of conditioning air in the air conditioning system. In this case, an additional duct is not necessary for the active noise reduction device because the duct of the air conditioning system can be also used for the active noise reduction device. However, when the active noise reduction device is intended for use with a particular apparatus, it is necessary to arrange a special duct for the active noise reduction device in the apparatus. Therefore, the overall size of the apparatus becomes larger and applications of the active noise reduction devices are limited.

In order to reduce a noise in a computer, it is possible to arrange an active noise reduction device within the computer, but this concept has not been realized since the active noise reduction device includes a duct which is to be incorporated in the casing of the apparatus along the path of the cooling air flowing in the casing. Conventionally, attempts to reduce noise in a computer have been directed to the design of the cooling fans so that the cooling fans themselves have a quiet structure. However, recent computers must be highly efficient and include many electronic components and a plurality of cooling fans for cooling the electronic components, so that the produced noise is high. In this situation, attempts to reduce noise by the design of the cooling fans cannot satisfy the requirements, and thus a further reduction in the noise is desired. Accordingly, the present invention aims to mount an active noise reduction device in a computer.

In some cases, it is desired to mount an active noise reduction device in a computer, for example, when the computer is arranged in a quiet office, and in some cases, it is not necessary to mount an active noise reduction device in a computer, for example, when the computer is arranged in a relatively noisy factory. If the active noise reduction device is fixedly incorporated in the computer, it is not easy to remove the active noise reduction device from the computer when the active noise reduction device is not necessary. Therefore, preferably, an active noise reduction device can be easily mounted in, and removed from, a computer. Also, it is desired that an active noise reduction device can be mounted on an existing computer.

SUMMARY OF THE INVENTION

The object of the present invention is to provide an active noise reduction device which can be easily mounted on and removed from an electronic apparatus.

Another object of the present invention is to provide an active noise reduction device which can be mounted on an electronic apparatus without the need for substantially changing the design of the electronic apparatus.

Another object of the present invention is to provide an electronic apparatus having an active noise reduction device mounted thereto for reducing the noise produced by the electronic apparatus.

According to the present invention, there is provided an active noise reduction device for reducing noise in an electronic apparatus having a casing and at least one element producing noise in the casing, said device comprising: a duct adapted to be mounted on the casing of the electronic apparatus and having at least one air passage formed therein, said at least one air passage having a first opening in communication with the interior of the casing and a second opening; a first detecting means arranged in the duct near the first opening for detecting sound; a controllable source of sound arranged in the duct near the second opening for making a sound to be superimposed on the noise introduced into the duct via said first opening; a second detecting means arranged in the duct near the second opening for detecting sound; and means for controlling the controllable source of sound, in response to outputs of said first and second detecting means, for reducing the noise induced in the casing.

Preferably, the first and second detecting means comprise microphones, and the controllable source of sound comprises a loud speaker.

Preferably, the duct comprises a plurality of passages arranged in parallel to each other, each of the passages including the first and second detecting means and the controllable source of sound.

Preferably, the duct is constructed such that the length of the at least one passage is variable. In this case, the duct may comprise a first duct unit adapted to be mounted to the casing of the electronic apparatus and having the first opening in communication with the interior of the casing, and a second duct unit slidablly coupled to the first duct unit so as to form the at least one passage by the first and second duct units. The first and second duct units together form the second opening.

Preferably, the first duct unit is adapted to be fixed to an outer panel of the casing of the electronic apparatus, or the first duct unit is adapted to form an integral part of an outer panel of the casing of the electronic apparatus.

Preferably, the duct is adapted to be mounted to the casing of the electronic apparatus in a vertical position, with the first opening located at an upper position and the second opening at a lower position.

Preferably, said means for controlling the controllable source of sound comprises a first control means receiving an output from the first detecting means and for delivering a control signal to the controllable source of the noise, and a second control means receiving an output from the second detecting means and for correcting the control signal based on the difference between the noise induced in the casing of the electronic apparatus and the sound made by the controllable source of sound. Preferably, said first control means receives an output from the first detecting means as well as a control signal directed to the controllable source of the noise.

The present invention also provides an electronic apparatus comprising: a casing; at least one electronic component arranged in the casing; at least one cooling fan arranged in the casing for cooling the at least one electronic component; and an active noise reduction device for reducing a noise produced by the cooling fan. The active noise reduction device comprises: a duct mounted on the casing of the electronic apparatus, the duct having at least one air passage formed therein, said at least one air passage having a first opening in communication with the interior of the casing and a second opening; a first detecting means arranged in the duct near the first opening for detecting a sound; a controllable source of sound arranged in the duct near the second opening for making a sound to be superimposed on the noise introduced in the duct via said first opening; a second detecting means arranged in the duct near the second opening for detecting a sound; and means for controlling the controllable source of sound, in response to outputs of said first and second detecting means, for reducing the noise induced in the casing.

BRIEF DESCRIPTION OF THE DRAWINGS

The present invention will become more apparent from the following description of the preferred embodiments, with reference to the accompanying drawings, in which.

DESCRIPTION OF THE PREFERRED EMBODIMENTS

Figure 1:
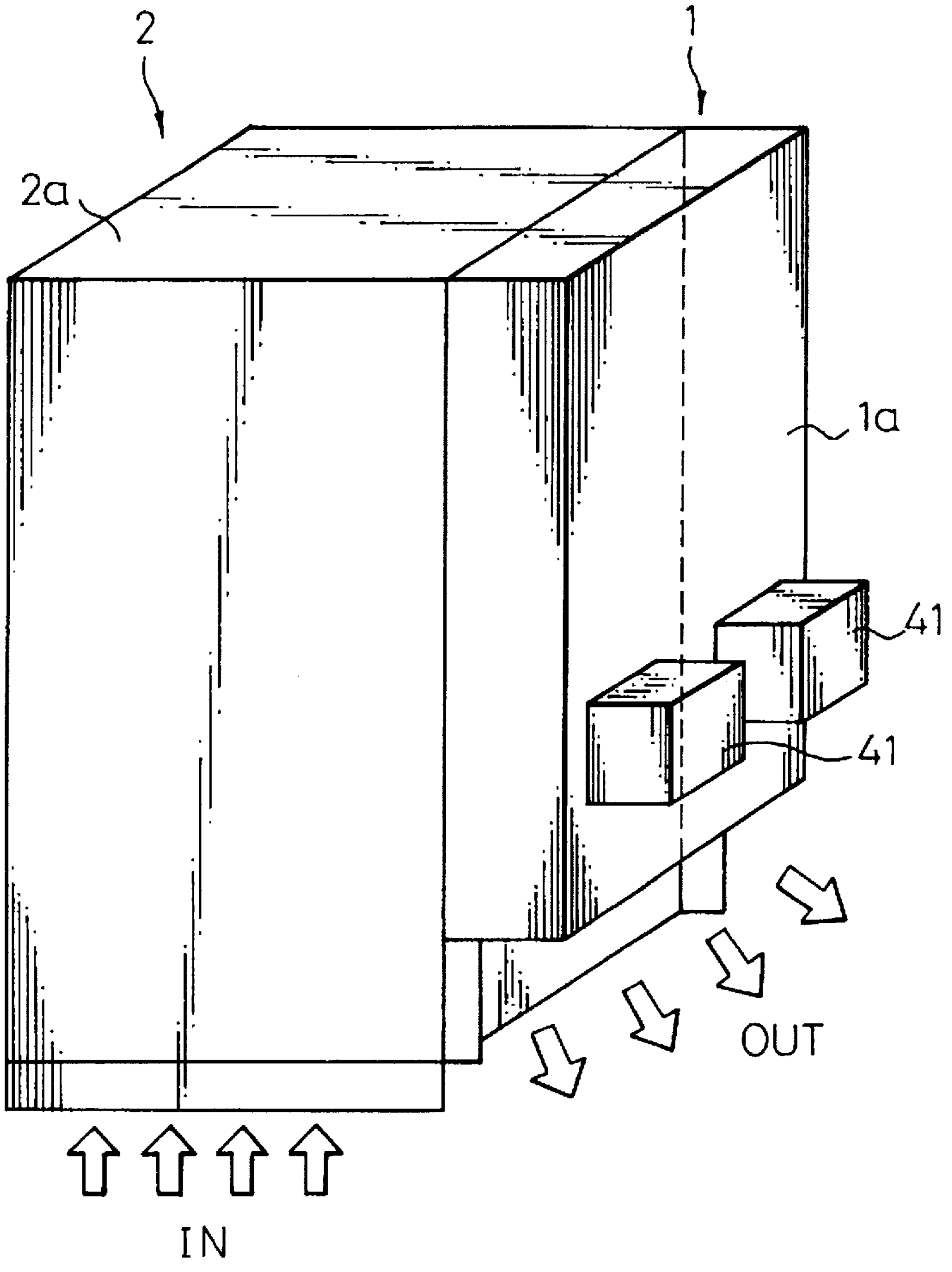
FIG. 1 is a diagrammatic perspective view of an active noise reduction device comprising a duct according to the embodiment of the present invention, the duct being mounted to a casing of an electronic apparatus.

FIG. 1 shows an active noise reduction device 1 comprising a duct 1*a* mounted on a casing (cabinet) 2*a* of an electronic apparatus 2 such as a computer. In the illustrated embodiment, the duct 1*a* is mounted on the rear panel of the casing 2*a*.

Figure 2:
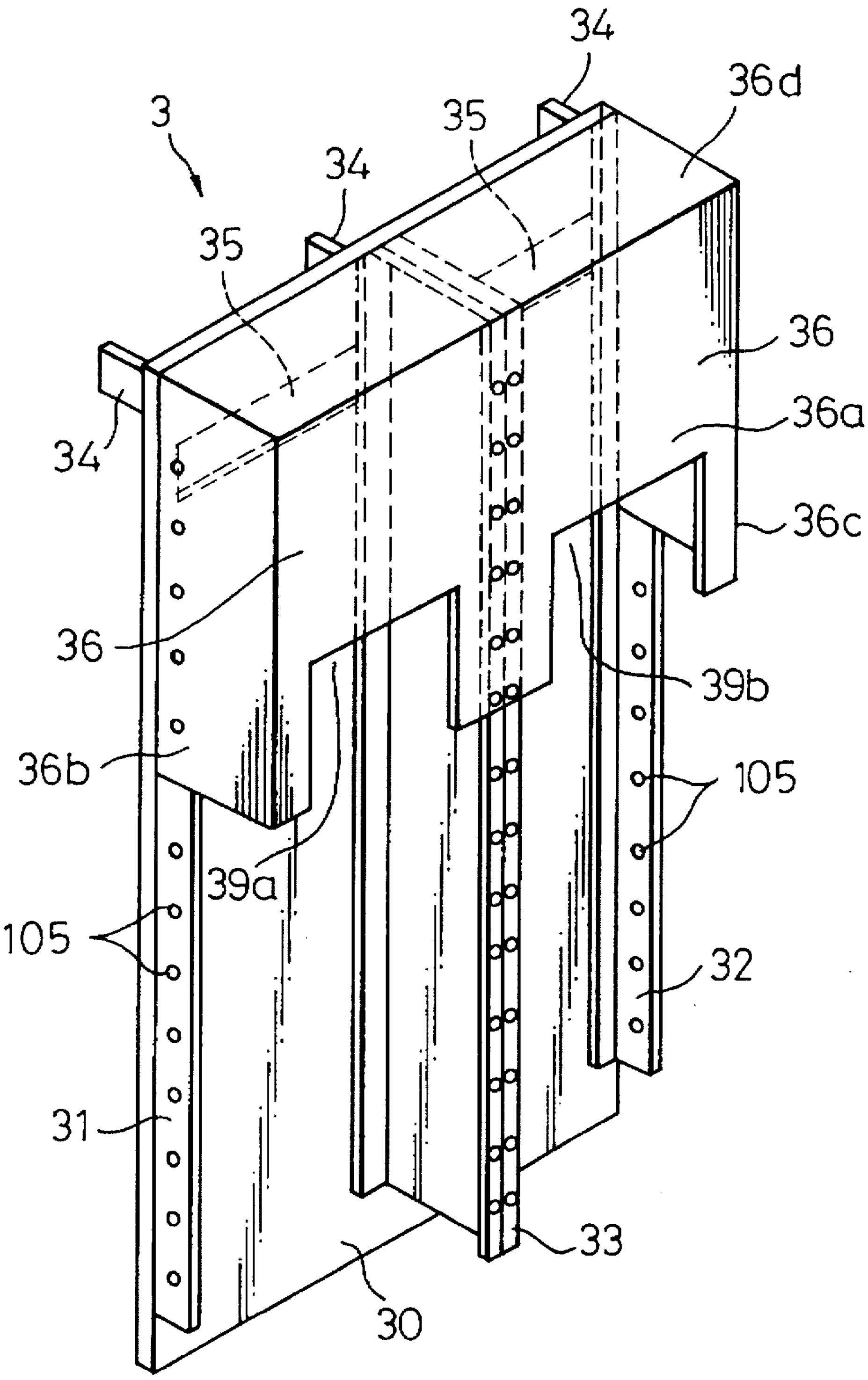
FIG. 2 is a perspective view of the first duct unit of the duct of the active noise reduction device.
Figure 3:
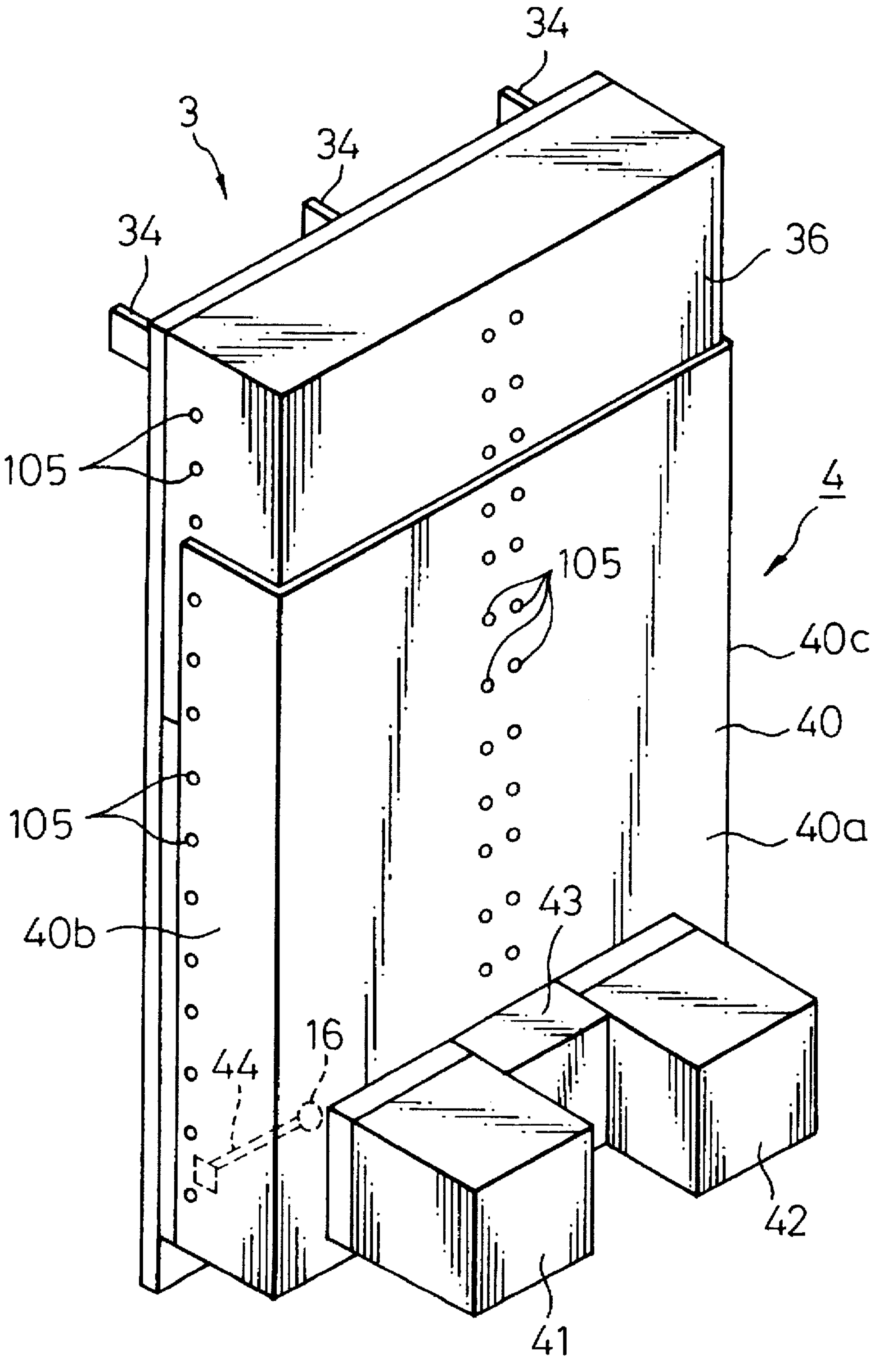
FIG. 3 is a perspective view of the duct with the second duct coupled to the first duct unit, the duct being in the fully extended position.
Figure 4:
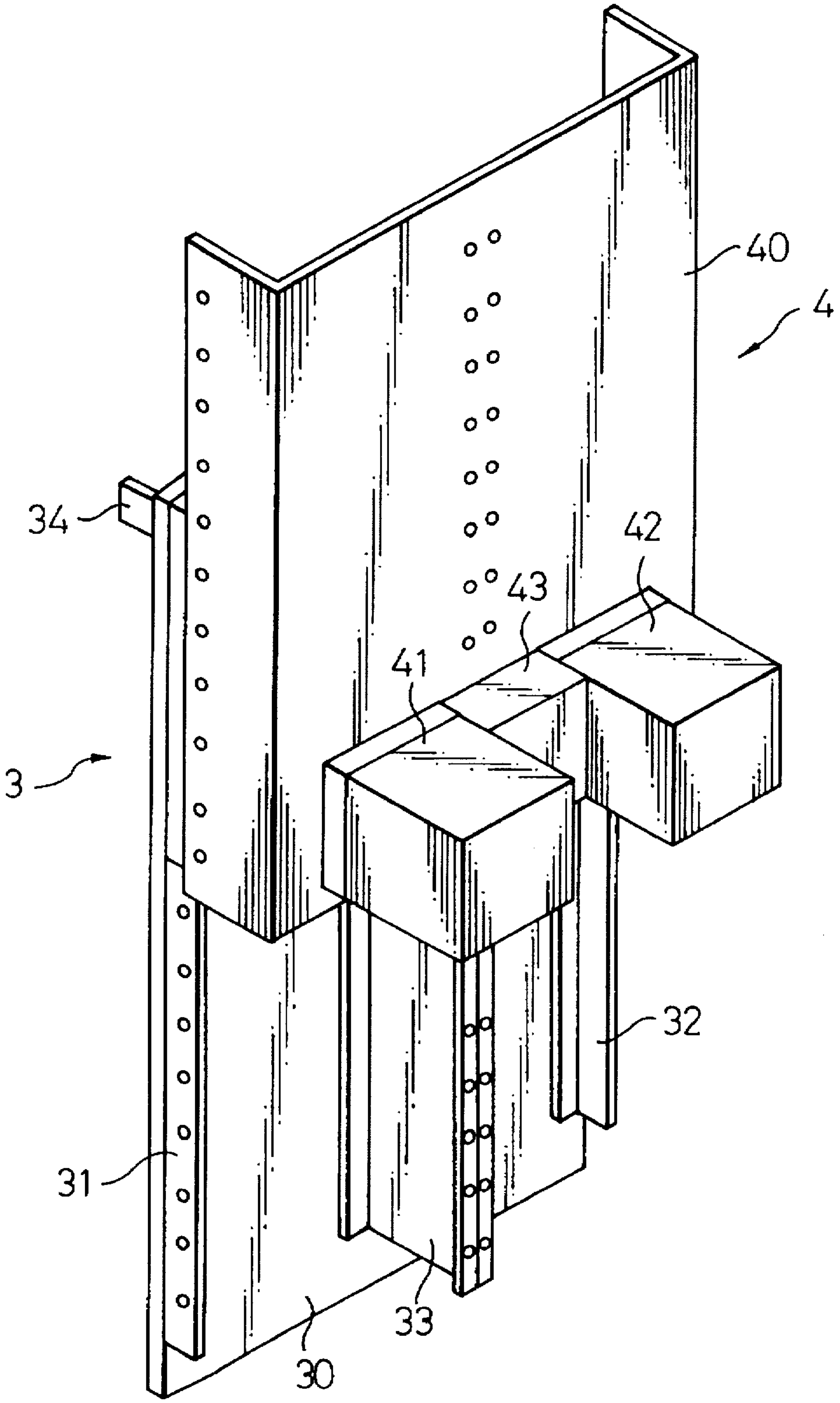
FIG. 4 is a perspective view of the duct in the shortened position.

The duct 1*a* comprises a first duct unit 3 shown in FIG. 2, and a second duct unit 4 shown in FIGS. 3 and 4. The first duct unit 3 is adapted to be mounted on the casing 2*a* of the electronic apparatus 2 and the second duct unit 4 is slidably coupled to the first duct unit 3. The duct 1 is constructed such that the effective length thereof is variable. FIG. 3 shows the duct 1*a* in the fully extended position, and FIG. 4 shows the duct 1*a* in the shortened position.

As shown in FIG. 2, the first duct unit 3 comprises a base plate 30, guide plates 31 and 32 vertically extending on the base plate 30 along the opposite edges thereof and a central separating plate 33 longitudinally extending between the guide plates 31 and 32.

A box-shaped cover 36 is fixed to the upper part of the base plate 30. The cover 36 comprises a front wall 36*a*, side walls 36*b* and 36*c*, and a top wall 36*d*. The front wall 36*a* extends parallel to the base plate 30, and extends to the opposite edges of the base plate 30 in line with the guide plates 31 and 32, respectively. The top wall 36*d* closes the top end of the cover 36, and the bottom end of the cover 36 is open. The central separating plate 33 extends to the top wall 36*d* of the cover 36 to divide the duct into two passages 39*a* and 39*b*.

Figure 7:
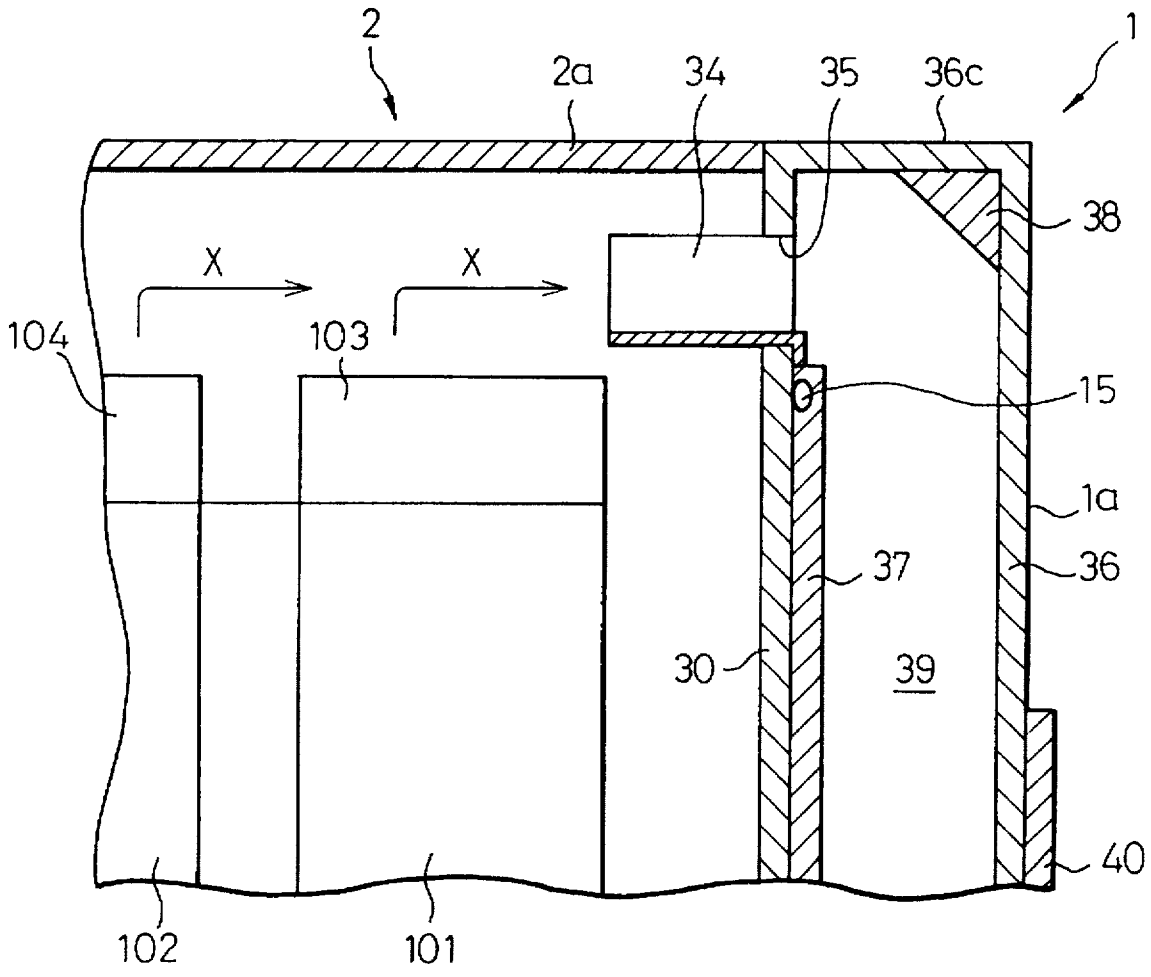
FIG. 7 is an enlarged cross-sectional view of a portion of the active noise reduction device and the casing of the apparatus of FIG. 5.

The base plate 30 has openings 35, one for each of the passages 39*a* and 39*b*. The openings 35 communicate with the interior of the casing 2*a* when the duct 1*a* is mounted on the casing 2*a*, as shown in FIG. 7. In FIG. 7, the base plate 30 also constitutes the rear panel of the casing 2*a* of the electronic apparatus 2, i.e., the base plate 30 is an integral part of the rear panel of the casing 2*a* of the electronic apparatus 2. Alternatively, in the embodiment of FIG. 9, the base plate 30 is fixed to the rear panel 2*b* of the casing 2*a*.

Figure 9:
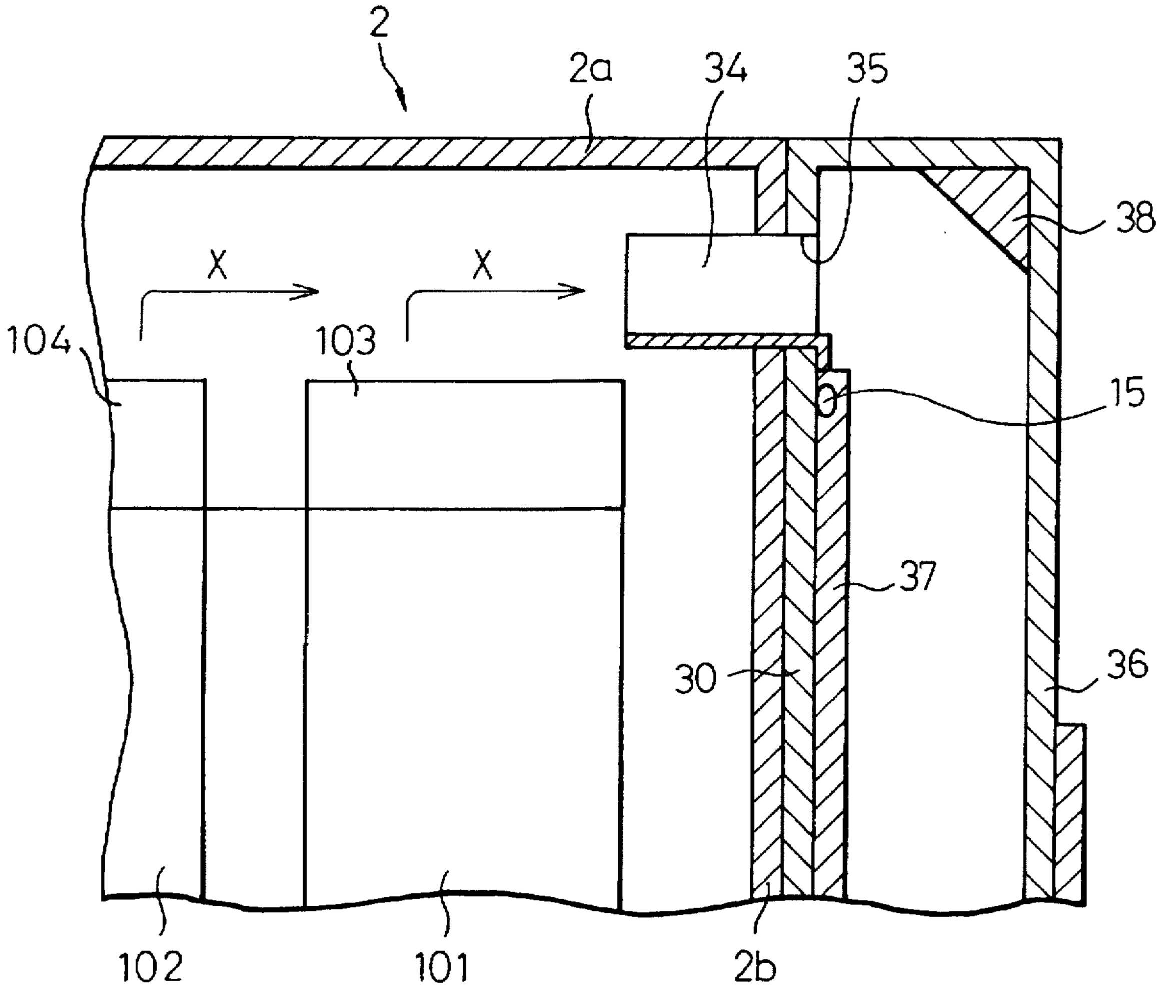
FIG. 9 is a cross-sectional view of the active noise reduction device and the casing of the apparatus according to another embodiment of the present invention.

In FIGS. 7 and 9, a plurality of electronic components 101 and 102, and a plurality of cooling fans 103 and 104 are arranged in the casing 2*a* of the computer. The cooling fans 103 and 104 draw air into the casing 2*a*, as shown by the arrow IN in FIG. 1, and cause air to flow through the casing 2*a*, as shown by the arrows X in FIGS. 7 and 9. The cooling fans 103 and 104 are arranged in the casing 2*a* at an upper position, and the openings 35 are arranged near the cooling fans 103 and 104 so that the cooling air enters the openings 35. A trough-shaped deflector plate 34 is attached to the base plate 30. A portion of the deflector plate 34 is anchored in the openings 35, and the remaining portion of the deflector plate 34 projects into the casing 2*a* toward the cooling fans 103 and 104 to prevent the cooling air from recirculating in the casing 2*a* and to guide the cooling air into the passages 39*a* and 39*b* in the duct 1*a*.

A sound absorbing material 37 is coated on the inner surface of the base plate 30, and a microphone 15 as a first detecting means is embedded in the sound absorbing material 37 near the openings 35. Also, a triangular cross-sectional sound absorbing material 38 is coated on the upper corner of the cover 36. Other sound absorbing material can be arranged as desired.

The second duct unit 4 comprises an U-shaped cover 40 having a front wall 40*a*, and side walls 36*b* and 36*c*. The top and the bottom of the U-shaped cover 40 are open. The U-shaped cover 40 is slidably fit on the cover 36 and the guide plates 31 and 32, to form with the first duct unit 3 the passages 39*a* and 39*b* therein. The bottom ends of the passages 39*a* and 39*b* are open. The second duct unit 4 is movable relative to the first duct unit 3 and thus the effective length of the passages 39*a* and 39*b* is variable. The first and second duct units 3 and 4 have vertical rows of holes 105 for receiving screws for fixing the second duct unit 4 to the first duct unit 3 at a desired relative position. The cooling air is finally discharged from the bottom openings of the passages 39*a* and 39*b*, as shown by the arrow OUT in FIG. 1.

Figure 5:
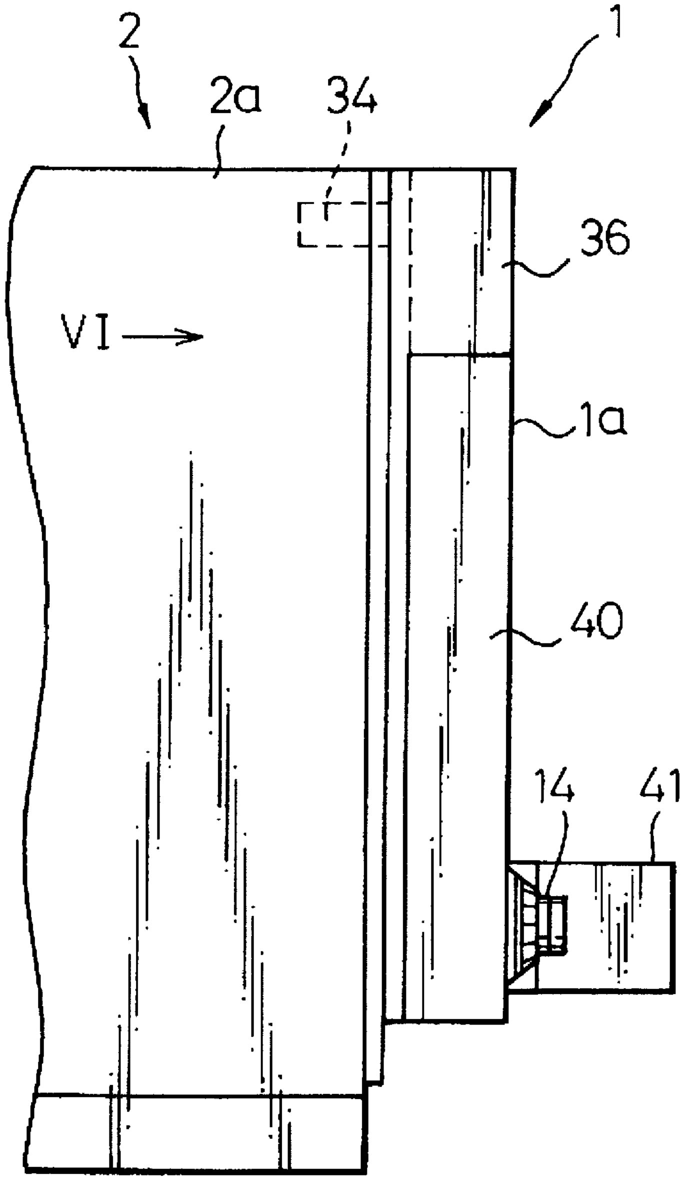
FIG. 5 is a side view of the active noise reduction device and the casing of the apparatus of FIG. 1.
Figure 6:
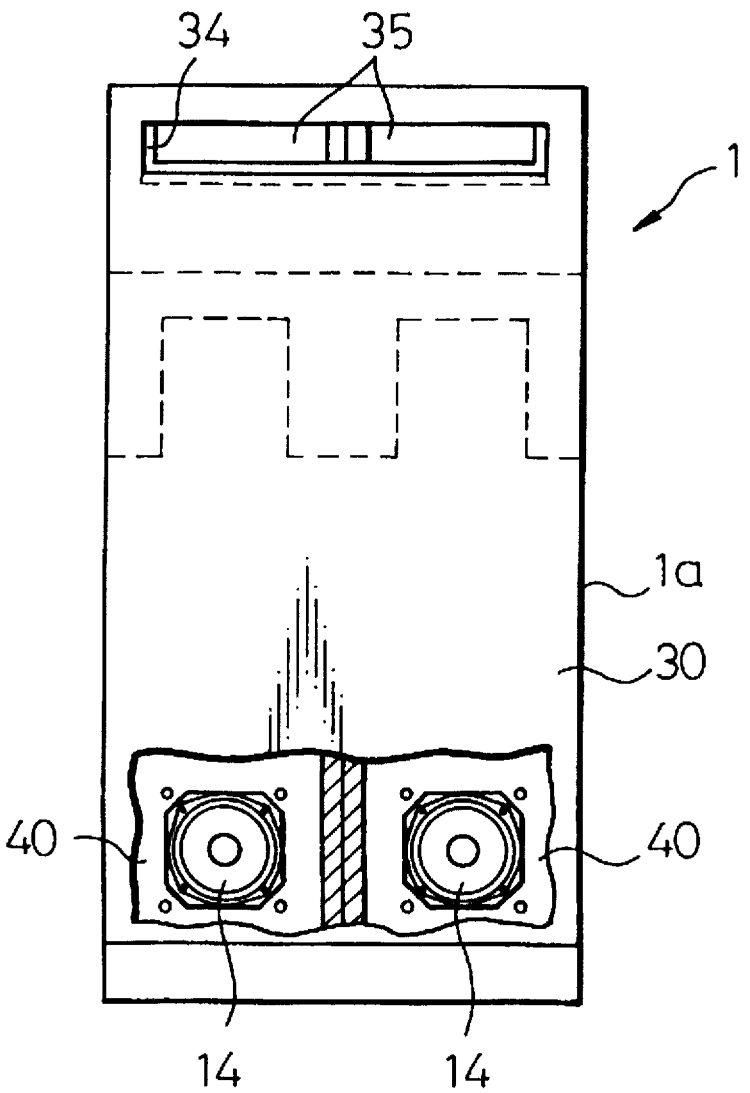
FIG. 6 is a front view of the active noise reduction device of FIG. 3, viewed in the direction of the arrow VI in FIG. 5.
Figure 8:
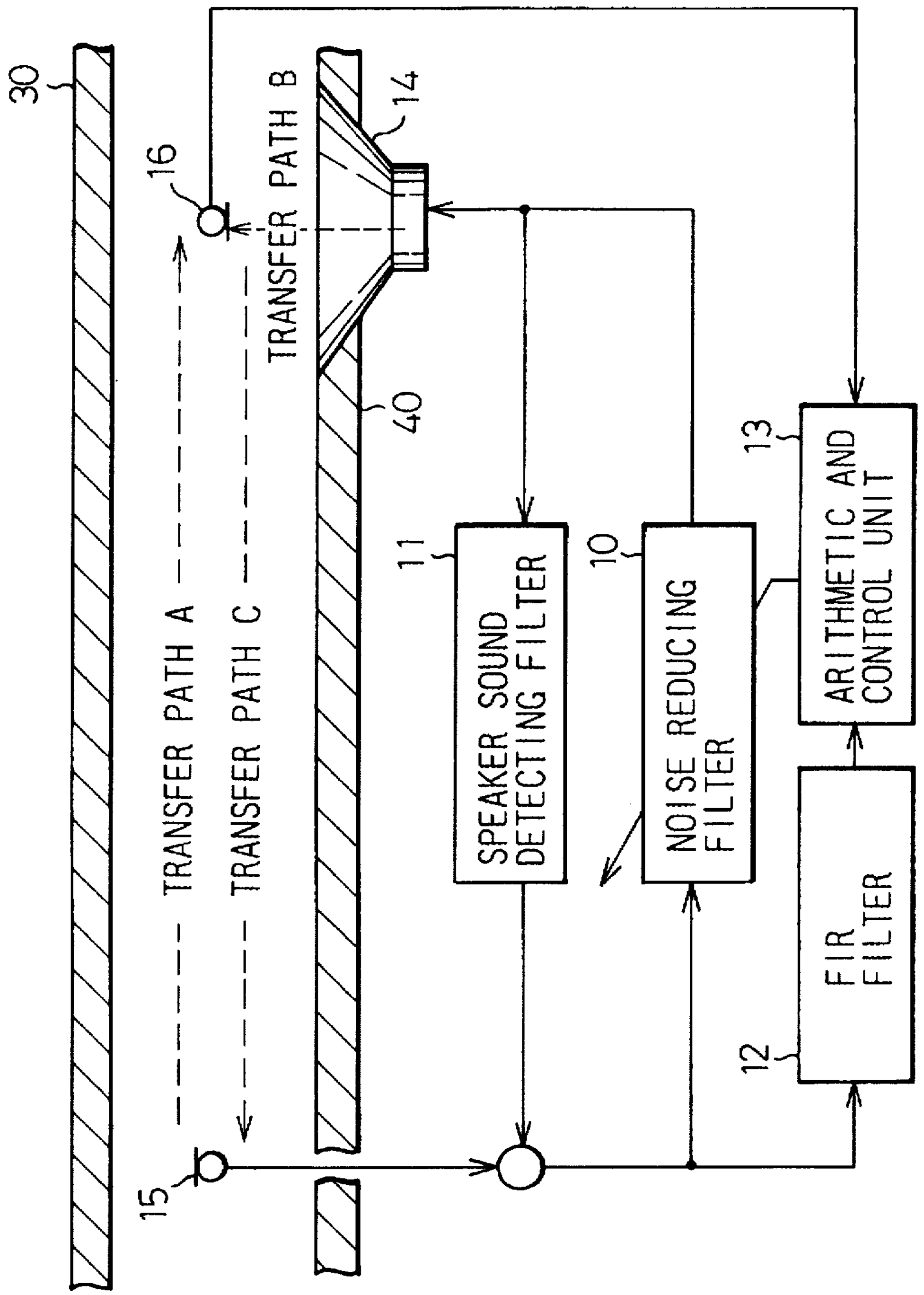
FIG. 8 is a block diagram of the control unit of the active noise reduction device.

Speaker boxes 41 and 42 including speakers 14 therein are arranged on the U-shaped cover 40 at the lower position, respectively. The speakers 14 are directed to the interior of the duct 1*a*, as shown in FIGS. 5 and 6. A control box 43 is arranged between the speaker boxes 41 and 42, as shown in FIG. 4. The control box 43 contains electrical components of the active noise reduction device 1 which are shown in FIG. 8. In addition, a microphones 16, as a second detecting means are arranged in front of the speaker boxes 41 and 42, respectively, passages 39*a* and 39*b*, as shown in FIG. 3. The microphones 16 are supported by respective support rods 44 which extend from the side walls 40*b* and 40*c*. The speakers 41 and 42 and the microphones 16 move with the second duct unit 40.

The transverse width of the passages 39*a* and 39*b* is determined depending on an upper limit frequency of a noise to be eliminated. Typically, an upper limit frequency is obtained from the relationship of f=C/2, where f is the frequency, L is the transverse width of the passage, and C is the sonic velocity. If the size of the passage is 28 mm×100 mm, the upper limit frequency of a noise which can be eliminated is 612 Hz.

FIG. 8 shows a block diagram in the control unit of the active noise reduction device 1 according to the embodiment of the present invention. The control unit comprises a noise reducing filter 10, a speaker sound detecting filter 11, an FIR filter 12, and an arithmetic and control unit 13. These components are housed in the control box 43. The speaker 14, the noise detecting microphone 15, and the sound error detecting microphone 16 are connected to these components.

Respective noise detecting microphones 15 are arranged in the passages 39*a* and 39*b*, near the, for detecting the noise produced by the electronic apparatus 2. The noise reducing filter 10 comprises an FIR filter for generating an electronic speaker control signal in response to outputs of the noise detecting microphone 15 so as to simulate the noise transfer path A.

The speaker 14 converts the electronic speaker control signal generated in the noise reducing filter 10 into an acoustic signal, i.e., a sound, which is superimposed on the noise propagating in the duct 1*a* according to the noise transfer path A. The sound error detecting microphone 16 detects the sound difference (=noise–emanated sound) and the output of the sound error detecting microphone 16 is input into the arithmetic and control unit 13 for correcting the filter coefficients in the noise reducing filter 10.

The FIR filter 12 is a filter simulating the transfer path B starting from the output of the noise reducing filter 10, through the sound error detecting microphone 16, to the sound error input of the noise reducing filter 10. The FIR filter 12 is provided to deal with the influence of the transfer path B based on a Filtered-X algorithm. If the transfer path B is not considered, it is not possible to exactly superimpose the control sound on the noise.

The arithmetic and control unit 13 corrects the filter coefficients in the noise reducing filter 10 based on the outputs of the FIR filter 12 and of the sound error detecting microphone 16.

The speaker sound detecting filter 11 is a filter simulating the transfer path C extending in reverse to the noise transfer path A. In the active noise reduction device 1, the sound made by the speaker 14 reaches the noise detecting microphone 15 via the transfer path C, and the noise detected by microphone 15 includes the component of the sound made by the speaker 14. Therefore, the speaker sound detecting filter 11 simulates this transfer path C to generate a signal corresponding to the sound made by the speaker 14 and this signal is subtracted from the signal detected by the noise detecting microphone 15.

In use, the active noise reduction device 1 is mounted to the rear of the casing 2*a* of the electronic apparatus 2, and the second duct unit 4 is set to make the duct 1*a* long, as shown in FIG. 3. If the initial length of the passages 39*a* and 39*b* is long, it is easier to determine the coefficients of the filters in the control unit. Therefore, it is preferable to start with the longest length of the passages 39*a* and 39*b* so that the coefficients of the filters in the control unit may converge. After this adjustment, the second duct unit 4 is moved slightly, relatively to the first duct unit 3, to shorten the length of the passages 39*a* and 39*b*, and the adjustment is again carried out. The adjusting operation is repeated until the coefficients of the filters in the control unit become optimum values in the condition where the length of the passages 39*a* and 39*b* is as short as possible, as shown in FIG. 4. The active noise reduction device 1 can thus work well with the shortest duct. If the length of the passages 39*a* and 39*b* is long, the number of the taps of the filters in the control unit increases and a considerable time is required for the device to learn and calculate the coefficients. It is, therefore, preferable to set the length of the passages as short as possible so as to improve the noise reduction. In this regard, the variable duct can establish the most efficient noise reduction.

In operation, the cooling fans 103 and 104 cause hot air to flow from the casing 2*a* of the electronic apparatus 1 into the duct 1*a* of the active noise reduction device 1 via the openings 35. At the same time, the noise produced in the casing 2*a* of the electronic apparatus 1 (including several sound components such as a noise of the motors of the cooling fan, a noise of vibrating elements, and a noise of the flowing air) leaks into the duct 1*a* of the active noise reduction device 1 via the openings 35. This noise is detected by the noise detecting microphone 15 and the output of the latter is input to the noise reducing filter 10 to generate a speaker control signal while the noise propagates in the duct 1*a* toward the speaker 14, and the speaker 14 makes a sound which is superimposed on the noise.

It is preferable that the duct 39 is arranged on the rear of the casing 2*a* of the electronic apparatus 2 in the vertical position so that the air flows from the top of the duct 1*a* to the bottom of the duct 1*b*, as shown in the embodiment, so that it is possible to mount the active noise reduction device 1 within the predetermined height of the casing 2*a* of the electronic apparatus 2 without substantially increasing the size of the overall structure of the apparatus. It is, however, possible to arrange the active noise reduction device on the other side or on the top of the casing 2*a* of the electronic apparatus 2. Also, the active noise reduction device is arranged on the air outlet of the casing 2*a* of the electronic apparatus 2 in the embodiments, but it is possible to arrange the active noise reduction device on the air inlet of the casing 2*a* of the electronic apparatus 2.

Various modifications can be made within the scope of the present invention. For example, the upper limit frequency of the noise to be reduced is limited by the transverse width of the duct. When it is desired to reduce the noise having a wide range of frequency, it is necessary to select a relatively narrow duct to allow the upper limit frequency to be raised. In this case, if the amount of the cooling air is large in the larger computer apparatus, and it is requested that the duct has a large cross sectional area, it is advisable to arrange two narrow passages 39*a* and 39*b* in the side-by-side relationship, as described in the above described embodiments. However, if the amount of air is small, it is possible that the duct has only one passage. In the other applications, it is possible that the duct has more than two passages, and the passages can be superimposed one on the other. In this case, the speaker of the inner passage can be attached to the lateral wall of the passage.

The active noise reduction device has preferably an extendable duct 1*a* as illustrated in the embodiments, but the active noise reduction device can have a duct of a fixed length. In the latter case, the structure of the device is further simplified, and in this case, the sound error detecting microphone can as well as the noise detecting microphone can be embedded in the base plate.

As explained in greater detail, according to the present invention, it is possible to mount the active noise reduction device on the casing of the electronic apparatus in a simple manner or to remove the active noise reduction device from the casing of the electronic apparatus, whereby it is possible to reduce the noise induced in the casing of the electronic apparatus by the active noise reduction device to provide a good working environment in the office. It is also possible to mount the active noise reduction device to the casing of the existing electronic apparatus without changing the substantial structure of the latter.

We claim:

1. An active noise reduction device for reducing noise in an electronic apparatus having a casing, the casing having an interior, and at least one element producing noise in the interior of the casing, said device comprising:

a duct adapted to be mounted on the casing of the electronic apparatus and having at least one air passage therein, said at least one air passage having a first opening in communication with the interior of the casing and a second opening;

first detecting means arranged in the duct near the first opening for detecting sound;

a controllable source of sound arranged in the duct near the second opening for producing sound to be superimposed on the noise introduced in the duct via said first opening;

second detecting means arranged in the duct near the second opening for detecting sound; and means for controlling the controllable source of sound in response to outputs of said first and second detecting means thereby to reduce the noise produced in the casing of the electronic apparatus, wherein said duct is adjustable thereby to vary the length of the at least one passage, and wherein said duct comprises a first duct unit adapted to be mounted on the casing of the electronic apparatus with the first opening in communication with the interior of the casing and a second duct unit slidably coupled to the first duct unit and together therewith forming the at least one passage.

2. An active noise reduction device according to claim 1, wherein said first and second detecting means comprise microphones, and said controllable source of sound comprises a speaker.

3. An active noise reduction device for reducing noise in an electronic apparatus having a casing, the casing having an interior, and at least one element producing noise in the interior of the casing, said device comprising:

a duct adapted to be mounted on the casing of the electronic apparatus and having at least one air passage therein, said at least one air passage having a first opening in communication with the interior of the casing and a second opening;

first detecting means arranged in the duct near the first opening for detecting sound;

a controllable source of sound arranged in the duct near the second opening for producing sound to be superimposed on the noise introduced in the duct via said first opening;

second detecting means arranged in the duct near the second opening for detecting sound; and means for controlling the controllable source of sound in response to outputs of said first and second detecting means thereby to reduce the noise produced in the casing of the electronic apparatus, wherein said first and second detecting means comprise microphones, and said controllable source of sound comprises a speaker, and wherein said duct comprises a plurality of passages arranged in parallel with each other, each of said passages including respective said first and second detecting means and respective said controllable source of sound.

4. An active noise reduction device according to claim 1, wherein said first and second duct units together form the second opening.

5. An active noise reduction device according to claim 1, wherein said first duct unit is adapted to be fixed to an outer panel of the casing of the electronic apparatus.

6. An active noise reduction device according to claim 1, wherein said first duct unit is adapted to form an integral part of an outer panel of the casing of the electronic apparatus.

7. An active noise reduction device according to claim 1, wherein said duct is adapted to be mounted on the casing of the electronic apparatus in a vertical position, with said first opening located at an upper position and said second opening at a lower position.

8. An active noise reduction device according to claim 1, wherein said means for controlling the controllable source of sound comprises first control means for receiving and responding to an output from the first detecting means and for producing and delivering a control signal to the controllable source of the noise, and a second control means for receiving and responding to an output from the second detecting means and for correcting the control signal based on the difference between the noise produced in the casing of the electronic apparatus and the sound produced by the controllable source of sound.

9. An active noise reduction device according to claim 8, wherein said first control means receives an output from the first detecting means as well as the control signal for the controllable source of the noise.

10. An electronic apparatus comprising:

a casing having an interior;

at least one electronic component arranged in the casing;

at least one cooling fan arranged in the casing for cooling the at least one electronic component and producing noise in the casing interior;

an active noise reduction device for reducing the noise produced in the casing by the at least one cooling fan, said active noise reduction device comprising:

a duct mounted on the casing of the electronic apparatus, the duct having at least one air passage formed therein, said at least one air passage having a first opening in communication with the interior of the casing and a second opening;

first detecting means arranged in the duct near the first opening for detecting sound in the casing interior;

a controllable source of sound arranged in the duct near the second opening for producing sound to be superimposed on the noise introduced into the duct via said first opening;

second detecting means arranged in the duct near the second opening for detecting sound; and means for controlling the controllable source of sound in response to outputs of said first and second detecting means for reducing the noise produced in the casing, wherein said duct is adjustable thereby to vary the length of the at least one passage, and wherein said duct comprises a first duct unit adapted to be mounted on the casing of the electronic apparatus and having the first opening in communication with the interior of the casing and a second duct unit slidably coupled to the first duct unit and defining therewith the at least one passage.

11. An electronic apparatus according to claim 10, wherein said cooling fan is arranged above the electronic component, and said duct is mounted on the casing of the electronic apparatus in a vertical position, with said first opening located at an upper position near said cooling fan and said second opening at a relatively lower position.

12. An electronic apparatus according to claim 11, further comprising a deflector disposed at said first opening and extending toward the cooling fan and guiding a flow of air to said first opening.

13. An electronic apparatus according to claim 10, wherein said first and second detecting means comprise respective microphones, and said controllable source of sound comprises a speaker.

14. An electronic apparatus comprising:

a casing having an interior;

at least one electronic component arranged in the casing;

at least one cooling fan arranged in the casing for cooling the at least one electronic component and producing noise in the casing interior;

an active noise reduction device for reducing the noise produced in the casing by the at least one cooling fan, said active noise reduction device comprising:

a duct mounted on the casing of the electronic apparatus, the duct having at least one air passage formed therein, said at least one air passage having a first opening in communication with the interior of the casing and a second opening;

first detecting means arranged in the duct near the first opening for detecting sound in the casing interior;

a controllable source of sound arranged in the duct near the second opening for producing sound to be superimposed on the noise introduced into the duct via said first opening;

second detecting means arranged in the duct near the second opening for detecting sound; and means for controlling the controllable source of sound in response to outputs of said first and second detecting means for reducing the noise produced in the casing, wherein said first and second detecting means comprise respective microphones, and said controllable source of sound comprises a speaker, and wherein said duct comprises a plurality of passages arranged in parallel to each other, and said electronic apparatus further comprises plural ones of said first and second detecting means and said plural controllable sources of sound respectively associated with and disposed in said plurality of passages.

15. An electronic apparatus according to claim 10, wherein said first and second duct units together form the second opening.

16. An electronic apparatus according to claim 15, wherein said first duct unit is fixed to a wall of the casing of the electronic apparatus.

17. An electronic apparatus according to claim 15, wherein said first duct unit is an integral part of a wall of the casing of the electronic apparatus.

18. An active noise reduction device according to claim 1, wherein said first detecting means is attached to the first duct unit, and said controllable source of sound and said second detecting means are attached to the second duct unit.

19. An active noise reduction device according to claim 10, wherein said first detecting means is attached to the first duct unit, and said controllable source of sound and said second detecting means are attached to the second duct unit.

* * * * *

UNITED STATES PATENT AND TRADEMARK OFFICE

CERTIFICATE OF CORRECTION

PATENT NO. : 5,636,286

DATED : June 3, 1997

INVENTOR(S) : MAKABE et al.

It is certified that error appears in the above-indentified patent and that said Letters Patent is hereby corrected as shown below:

Col. 1, line 26, change "reduce a noise" to --reduce noise--.

Col. 5, line 14, delete "a" (first occurrence);
line 16, after "respectively," insert --in the--;
line 24, change "f=C/2," to --f=C/2L,--;
line 38, after "near the" insert --correspondig openings 35 thereof--.

Signed and Sealed this

Thirtieth Day of September, 1997

Attest:

BRUCE LEHMAN

Attesting Officer

*Commissioner of Patents and Trademarks*